United States Patent [19]

Kurono et al.

[11] Patent Number: 4,870,062
[45] Date of Patent: Sep. 26, 1989

[54] ORGANO-PLATINUM COMPLEX AND USE THEREOF AS ANTI-TUMOR AGENT

[75] Inventors: Masayasu Kurono; Ryoichi Unno; Yukiharu Matsumoto; Yasuaki Kondo; Takahiko Mitani; Takahito Jomori; Hisashi Michishita; Kiichi Sawai, all of Aichi, Japan

[73] Assignee: Sanwa Kagaku Kenkyusho Co., Ltd., Aichi, Japan

[21] Appl. No.: 183,575

[22] Filed: Apr. 19, 1988

[30] Foreign Application Priority Data

Apr. 23, 1987 [JP] Japan .................................. 62-98676

[51] Int. Cl.⁴ ..................... A61K 31/695; C07F 15/00
[52] U.S. Cl. ...................................... 514/63; 514/492; 586/137; 586/12
[58] Field of Search .................. 514/492, 63; 556/9, 556/12, 137

[56]  References Cited
U.S. PATENT DOCUMENTS 4,500,465  2/1985  Amundsen et al. ................ 556/137

OTHER PUBLICATIONS

Nature, vol. 222, Apr. 26, 1969, pp. 385–386, Platinum Compounds: A New Class of Potent Antitumor Agent.

*Primary Examiner*—Donald B. Moyer
*Assistant Examiner*—Stuart L. Hendrickson
*Attorney, Agent, or Firm*—Armstrong, Nikaido, Marmelstein, Kubovcik & Murray

[57]  ABSTRACT

A removable rating plug for a circuit breaker provides an active variable impedance in series with a reference resistor between the sensing terminals of the circuit breaker trip circuit to adjust the sensing voltage produced in response to the input current received from current monitors in the protected circuit. The active variable impedance, which is energized by the input current, includes a high gain transistor amplifier, preferably a Darlington transistor, controlled by an operational amplifier. A control circuit includes a pair of reference diodes which match the forward drop across the Darlington transistor when full on, in series with a reference voltage selection circuit which applies a reference voltage to the non-inverting input of the operational amplifier. The voltage at the connection between the Darlington transistor and the reference resistor is fed back to the inverting input of the operational amplifier so that the gain of the amplifier, and therefore the variable impedance in series with the reference resistor, varies with the reference voltage.

22 Claims, No Drawings

ORGANO-PLATINUM COMPLEX AND USE THEREOF AS ANTI-TUMOR AGENT

BACKGROUND OF THE INVENTION

1. Field of the Invention

The present invention relates to novel organo-platinum complexes and an anti-tumor composition containing at least one of the complexes as an effective ingredient therefor.

2. Related Arts

It has been known that certain organo-platinum complexes show an anti-tumor activity. Since the fact that cis-dichlorodiamine platinum (II) (General term: Cisplatin) has anti-tumor activity was reported by B. Rosenberg et al ["Nature" Vol. 222, page 385 (1969)], various studies have been energitically made to develop various organo-platinum complexes per se or to establish a new chemotherapy system on tumors and more particularly cancers. As a result, for instance, following organo-platinum complexes have been proposed.

(a) Malonato(1,2-diaminocyclohexane)platinum (II) [Jap. Pat. No. 53-31648 (A)], (b) Sulfato(1,2-diaminocyclohexane)platinum (II) [Jap. Pat. No. 54-44620 (A)], (c) 4-Carboxyphthalato(1,2-diaminocyclohexane)-platinum (II) [Jap. Pat. No. 54-46752 (A)], and (d) cis-Dichloro-trans-dihydroxy-bis(isopropylamine)-platinum (II) [Jap. Pat. No. 54-77694 (A)].

Each of such known organo-platinum complexes has advantages of showing an excellent anti-tumor action, having a wide anti-tumor spectrum and having a good solubility to water, but shows a disadvantage of having a relatively high side effect. For instance, the Cisplatin which is one of examplar conventional organo-platinum complexes shows a high nephrotoxicity, may accompany a violent nausea or vomiting, when the complex is dosed, and eventually causes dysacousis.

In order to suppress a generation of such side effects, and more particularly the nephrotoxicity or reduce a symptom due to this side effect, hitherto, various measures have been adopted in dosing manner of the organo-platinum complex, for instance the Cisplatin was mixed with mannitol, dextrose or the like, or dosed together with a diuretic drug such as phlocemide. However, each of such measures is a passive one and is not preferable, since its effect will be influenced by difference in each individual.

SUMMARY OF THE INVENTION

A basic object of the invention is, therefore to provide a novel organo-platinum complex which shows a relatively high anti-tumor activity and weak side effect and more particularly in nephrotoxicity.

Another object of the invention is to provide an anti-tumor composition containing the complex, as an effective ingredient.

Accordiing to the invention, such objects and other objects which shall be appreciated by more fully understanding the invention can be attained by an organo-platinum complex having a silicon-containing diamine as ligand and represented by the following general formula.

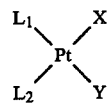
(I)

wherein X and Y have the same meaning of a halogen, oxyanion or carboxylate, respectively or X is a oxyanion or dicarboxylate together with Y, and $L_1$ and $L_2$ are bonded together to form one of silicon containing diamine compounds selected from the group consisting of

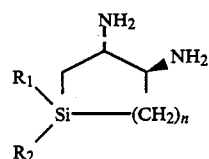
(II)

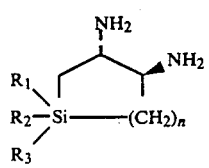
(III)

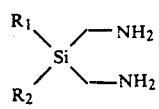
(IV)

in which $R_1$, $R_2$ and $R_3$ are a lower alkyl or phenyl, respectively, and n is an integer of 0 to 1.

An anti-tumor composition according to the invention is characterized by comprising as an effective ingredient at least one of the complexes shown by said Formula (I) in an effective amount, together with a pharmaceutically acceptable carrier.

In connection with the complexes shown by said Formula (I), the definition of each substituent shall be given as follows. The term of halogen may be of chlorine, bromine or iodine. As the oxyanion, sulfate, nitrate, selenite or the like may be listed. As the carboxylate, chloroacetate, pyruvate, glucolate or the like may be listed. As the dicarboxylate, oxalate, malonate, hydroxymalonate, carboxyphthalate, 1,1-cyclobutanedicarboxylate or the like may be listed. The lower alkyl may be of straight-chain or branched-chain alkyl groups having 1 to 5 carbon atoms, for instance methyl, ethyl, propyl, isopropyl, butyl, isobutyl, pentyl and the like.

The organo-platinum complexes (I) according to the invention can be prepared by utilizng various methods known per se, for instance, as stated below.

(a) Complexes (I), wherein X and Y are halogen atom, respectively:

The complex can be prepared by reacting a halogenated platinic acid salt with the compound II, III or IV.

As the halogenated platinic acid salt, lithium salt, potassium salt, sodium salt or the like may be listed, but the potassium salt is preferable. Among the other reactant, trans-1,2-diamino-4,4-dimethyl-4-silacyclopentane, trans-1,2-diamino-4,4-dimethyl-4-silacyclohexane or the like may be listed as the compound II; trans-1,2-diamino-4-trimethylsilylpentane, trans-1,2-diamino-4-trimethylsilylhexane or the like may be listed as the compound III; and bis(aminomethyl)dimethylsilane or the like may be listed as the compound IV.

(b) Complexes (I), wherein X and Y are as oxyanion, carboxylate or dicarboxylate, respectively:

The complex can be prepared by reacting a complex to be obtained by the method (a), wherein X and Y are a halogen atom, respectively with a silver salt of an organic or inorganic acid. The complex (I), wherein X and Y are a carboxylate or dicarboxylate can also be prepared by reacting a complex, wherein X represents sulfate together with Y, with barium hydroxide and then reacting the resulting intermediate of dihydroxy platinum (II) with an organic or inorganic acid. Of course, it is preferable to carry out the reaction under a dark atmosphere, when the silver salt reagent is used.

Each of such reactions can be carried out in an aqueous solvent and the reaction proceeds smoothly at the room or elevated temperature. After completion of the reaction, precipitates are collected or the reaction solution is concentrated to dryness to afford the desired complex. In general, there is required no further purification but if necessary, the crude complex can be purified in a conventional manner, for instance through recrystallization with use of a suitable solvent such as water, ethanol or the like.

Among the starting materials for preparing the organo-platinum complexes (I), bis(aminomethyl)dimethylsilane belonging to the compound (IV) is known compound and is available from the market and otherwise, it may be synthesized in accordance with the method as disclosed in "Z. Anorg. Allgem, Chem." Vol. 317, pages 41 to 53 (1962). While each of the compounds (II) and (III) is novel compound not disclosed in any literature but can be synthesized as shown in the following reaction formula.

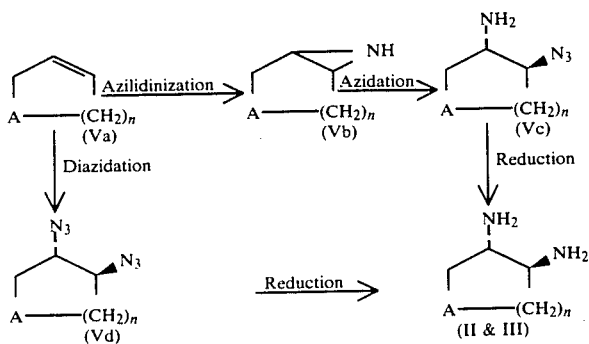

wherein A is a group of

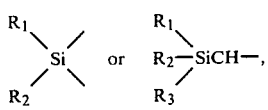

and $R_1$, $R_2$, $R_3$ and n have the meanings as referred to.

The starting material (Va) in the above identified reaction system has been known and can be obtained from the market and otherwise, may be synthesized in accordance with one of the methods disclosed in "J. Organomet. Chem." Vol. 63, pages 119–131 (1973) and Vol. 264, pages 127 to 133 (1984) as well as "Izv. Akad. Nauk SSSR, Ser. Khim" pages 1452 to 1953 (1977). Each of the compounds (Vb, Vc and Vd) can be prepared in accordance with methods known per se. For instance, the compound (Vb) can be synthesized by azilidinizing the compound (Va) in accordance with the method as disclosed in "J. Chem. Soc. Chem. Comm." pages 560 to 561 (1980), the compound (Vc) can be synthesized by azidizing the compound (Vb) in accordance with the method as disclosed in "J. Org. Chem." Vol. 32, pages 511 to 517 (1967), and the compound (Vd) can be synthesized by diazidizing the compound (Va) in accordance with the method as disclosed in "Tetrahedron Vol. 27, pages 4953 to 4963 (1971).

Further, each of the compounds (II and III) which can be employed as one of starting materials for preparing the organo-platinum complexes of the invention can be prepared by reducing the compound (Vc or Vd) through a catalytic hydrogenation or with use of a metal hydride.

In case of preparing an anti-tumor composition with use of at least one of the organo-platinum complexes, as effective ingredient(s), there is no limitation in its medicine form and thus it may be made into one for oral or non-oral administration. As for oral administration, tablet, capsule, granule, powder and the like. While as for non-oral administration, a solution and dry powder for injection and a suppository may exemplarily be listed. In connection with this, the medicine can be prepared in a conventional manner.

DETAILED DESCRIPTION OF THE PREFERRED EMBODIMENTS

The invention will now be further explained with reference to Reference Examples, Examples of preparing organo-platinum complexes, Pharmacological Test Examples as well as Examples for preparing medicines.

REFERENCE EXAMPLE 1

3,3-Dimethyl-6-aza-3-silabicyclo[3.1.0]hexane

To a solution of 40.0 g (0.212 mol) of p-toluenesulfonylhydroxylamine in 500 ml of methylene chloride was added 12.0 g (0.106 mol) of 1,1-dimethyl-1-silacyclopent-3-ene and the mixture was stirred at 4° C. for 64 hours.

The reaction mixture was concentrated in vacuo and the resulting residue was dissolved in 100 ml of water and extracted with ethyl ether (200 ml). The aqueous layer was neutralized with sodium bicarbonate, extracted with ethyl ether (100 ml×2), the ether layer was washed with water, dried over sodium sulfate and distilled out ethyl ether at the atmospheric pressure. Then the resulting residue was distilled under reduced pressure to afford 7.11 g (52.3%) of the desired compound as colorless oil.

Boiling point: 84°–85° C. (80 mmHg). HRMS (m/z): 127.0828 (M+, $C_6H_{13}NSi$; Calcd. 127.0817) 126.0762 (M-H, $C_6H_{12}NSi$; Calcd. 126.0739).

MS (EI/GC) m/z: 127 (M+), 126 (M-H), 112 (M-Me, base peak).

$^1$H-NMR (CDCl$_3$) δppm: 0.03 and 0.06 (each 3H, s, SiMe$_2$) 0.5–1.3 (4H, m,

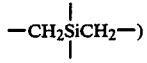

2.47 (2H, brs.,

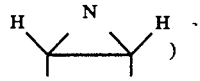
)

IR (KBr) cm$^{-1}$: 3340 (NH), 3000, 2950, 2910 (CH), 1550 (NH), 1250, 845 (C—Si).

REFERENCE EXAMPLE 2 trans-1-Amino-2-azido-4,4-dimethyl-4-silacyclopentane

A mixture of 7.00 g (55.1 mmol) of 3,3-dimethyl-6-aza-3-silabicyclo[3.1.0]hexane as obtained in Reference Example 1, 17.9 g (0.276 mol) of sodium azide and 17.4 g (0.276 mol) of ammonium chloride in 360 ml of a mixed solvent of ethanol-water (5:1) was refluxed for 1 hour. The reaction mixture was cooled and poured into ice-water (1 liter), extracted with ethyl ether (500 ml×3), the ethyl ether layer was washed with water, dried over sodium sulfate and evaporated in vacuo to afford 7.75 g (82.7%) of the desired compound as pale yellow oil.

MS (EI/GC) m/z: 171 (M+1), 155 (M-Me), 142 (M-N$_2$), 74 (base peak).

$^1$H-NMR (CDCl$_3$) δppm: 0.03 (6H, s, SiMe$_2$) 0.6-1.2 (4H, m,

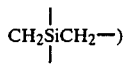

1.63 (2H, brs., -NH$_2$) 2.4-3.6 (2H, m,

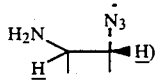

IR (KBr) cm$^{-1}$: 3400, 3330, (MH$_2$), 2960, 2900 (CH), 2100 (N$_3$), 1620 (NH$_2$), 1260, 845 (C—Si).

REFERENCE EXAMPLE 3 trans-1,2-Diamino-4,4-dimethyl-4-silacyclopentane

To a suspension of 3.35 g (88.2 mmol) of lithium aluminum hydride in 100 ml of anhydrous ethyl ether was added dropwise a solution of 7.50 g (44.1 mmol) of trans-1-amino-2-azido-4,4-dimethyl-4-silacyclopentane as obtained in Reference Example 2 in 100 ml of anhydrous ethyl ether with stirring at 5°-10 C. under argon atmosphere for 1.5 hours.

After stirring at room temperature for 2 hours, 3:35 ml of 15% sodium hydroxide and 13.4 ml of water were added dropwise to the reaction mixture and then the resulting precipitate was filtered off. The filtrate was dried over sodium sulfate, and distilled out ethyl ether at atmospheric pressure and the resulting residue was distilled under reduced pressure to afford 5.15 g (81.1%) of the desired compound as colorless oil.

Boiling point: 120° C. (40 mmHg).

HRMS (m/z): 144.1064 (M+, C$_6$H$_{16}$N$_2$Si; Calcd. 144.1082).

MS (EI/GC) m/z: 144 (M+), 129 (M-Me), 101, 86 (base peak).

$^1$H-NMR (CDCl$_3$) δppm: 0.00 (6H, s, SiMe$_2$) 0.2-1.2 (4H, m,

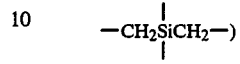

1.30 (4H, s, —NH$_2$×2) 2.3-2.7 (2H, m, C<u>H</u>—NH$_2$×2)

IR (KBr) cm$^{-1}$: 3340, 3260, 3180 (NH$_2$), 2940, 2880, 2840, (CH), 1660, 1580 (NH$_2$), 1250, 840 (C—Si).

REFERENCE EXAMPLE 4 trans-1,2-Diazido-4-trimethylsilylcyclohexane

To a solution of 1.24 g (6.43 mmol) of 4-trimethylsilylcyclohexene, 8.36 g (0.129 mol) of sodium azide, 35.7 g (0.129 mol) of iron (II) sulfate and 124 mg of iron (III) sulfate in 60 ml of a mixed solvent of acetone-water (1:1) was added dropwise 3.94 ml of 30% hydrogen peroxide with stirring at 0° to 5° C. for 30 minutes.

After stirring at 0° to 5° C. for 1 hour, the reaction mixture was diluted with water and extracted with ethyl ether (200 ml×2), the ether layer was washed with water, dried over sodium sulfate and evaporated in vacuo to afford 1.22 g (71.9%) of the desired compound as pale yellow oil.

MS (EI/GC) m/z: 223 (M-Me), 154 (M-2N$_3$), 73 (base peak).

$^1$H-NMR (CDCl$_3$) δppm: 0.00 (9H, s, SiMe$_3$) 0.6-2.8 (7H, m, —CH$_2$—×3, Si—CH—) 3.5-4.1 (2H, m, CH—N$_3$×2).

IR (KBr) cm$^{-1}$: 2930, 2960 (CH), 2090 (N$_3$), 1270 (C—Si).

REFERENCE EXAMPLE 5 trans-1,2-Diamino-4-trimethylsilylcyclohexane

To a suspension of 700 mg (18.5 mmol) of lithium aluminum hydride in 10 ml of anhydrous ethyl ether was added dropwise a solution of 1.10 g (4.61 mmol) of trans-1,2-diazido-4-trimethylsilylcyclohexane (as obtained in Reference Example 4) in 10 ml of anhydrous ethyl ether with stirring at 0° to 5° C. under argon atmosphere for 30 minutes.

After stirring at 0° to 5° C., for 1 hour, 0.70 ml of 15% sodium hydroxide and 2.80 ml of water were added dropwose to the reaction mixture and then the resulting precipitate was filtered off. The filtrate was dried over sodium sulfate and evaporated in vacuo. Then the resulting residue was distilled in vacuo to afford 560 mg (65.2%) of the desired compound as colorless oil.

Boiling point: 155° C. (35 mmHg).

MS (EI/GC) m/z: 186 (M+), 171 (M-Me), 128 (base peak).

$^1$H-NMR (CDCl$_3$) δppm: 0.00 (9H, s, SiMe$_3$) 0.7-2.4 (7H, m, —CH$_2$—×3, Si—CH—) 1.52 (4H, s, —NH$_2$×2) 2.5-2.8 (2H, m, CH—N×2).

IR (KBr) cm$^{-1}$: 3350, 3280 (NH$_2$), 2910, 2840 (CH), 1250 (C—Si).

EXAMPLE 1 cis-Dichloro(trans-1,2-diamino-4,4-dimethyl-4-silacyclopentane)platinum (II)

To a solution of 1.44 g (10.0 mmol) of trans-1,2-diamino-4,4-dimethyl-4-silacyclopentane (as obtained in Reference Example 3) in 30 ml of water was added 4.15 g (10.0 mmol) of potassium tetrachloroplatinate and the resulting mixture was stirred at 25° C. for 18 hours. The precipitate was filtered, washed with water and dried in vacuo to afford 3.88 g (94.6%) of the desired compound as yellow crystals.

Melting point: 310°–315° C. (dec.).

FAB-MS (m/z): 451, 452, 453 (M+41, $^{194}$Pt, $^{195}$Pt, $^{196}$Pt).

IR (KBr) cm$^{-1}$: 3440 (br.), 3260, 3200 (NH$_2$), 2950, 2850 (CH), 1630, 1560 (NH$_2$), 1250, 840 (C—Si).

Elementary analysis (C$_6$H$_{16}$Cl$_2$N$_2$SiPt): Cal.: C, 17.56; H, 3.93; N, 6.83. Found: C,, 17.75; H, 3.95; N, 6.68.

EXAMPLE 2 cis-Dichloro(trans-1,2-diamino-4,4-dimethyl-4-silacyclohexane)platinum (II)

This compound was prepared by the similar procedure as in the case of Example 1, except for the treatment with trans-1,2-diamino-4,4-dimethyl-4-silacyclohexane (1.58 g, 10.0 mmol) instead of trans-1,2-diamino-4,4-dimethyl-4-silacyclopentane. The yield was 3.64 g (85.9%) as yellow crystals.

Melting point: 300°–310° C. (dec.).

IR (KBr) cm$^{-1}$: 3440, 3264, 3192 (NH$_2$), 2916 (CH), 1555 (NH$_2$), 1254, 845 (C-Si).

Elementary analysis (C$_7$H$_{18}$Cl$_2$N$_2$SiPt): Cal.: C, 19.81; H, 4.28; N, 6.60. Found: C, 19.96; H, 4.30; N, 6.22.

EXAMPLE 3 cis-Dichloro(trans-1,2-diamino-4-trimethylsilylcyclohexane)platinum (II)

This compound was prepared by the similar procedure as in the case of Example 1, except for the treatment with trans-1,2-diamino-4-trimethylsilylcyclohexane (1.86 g, 10.0 mmol) in stead of trans-1,2-di-amino-4,4-dimethyl-4-silacyclopentane. The yield was 3.32 g (73.5%) as yellow crystals.

Melting point: 290°–300° C. (dec.).

IR (KBr) cm$^{-1}$: 3435, 3255 (NH$_2$), 3195, 3105, 2935, 2855 (CH), 1252 (C-Si).

Elementary analysis (C$_9$H$_{22}$Cl$_2$N$_2$SiPt): Cal.: C, 23.89; H, 4.90; N, 6.19. Found: C, 27.87; H, 5.61; N, 6.06.

EXAMPLE 4 cis-Dichloro[bis(aminomethyl)dimethylsilane]platinum (II)

This compound was prepared by the similar procedure as in the case of Example 1, except for the treatment with bis(aminomethyl)dimethylsilane (1.18 g, 10.0 mmol) instead of trans-1,2-diamino-4,4-dimethyl-4-silacyclopentane. The yield was 3.16 g (82.3%) as yellow crystals.

Melting point: 270°–300° C. (dec.).

IR (KBr) cm$^{-1}$: 3440, 3236, 3204 (NH$_2$), 2952, 2888 (CH), 1602 (NH$_2$), 1257, 850 (C—Si).

Elementary analysis (C$_4$H$_{14}$Cl$_2$N$_2$SiPt): Cal.: C, 1250; H, 3.67; N, 7.29. Found: C, 12.46; H, 3.71; N, 7.11.

EXAMPLE 5

Sulfato(trans-1,2-diamino-4,4-dimethyl-4-silacyclopentane)platinum (II)

To a suspension of 2.05 g (5.00 mmol) of cis-dichloro(trans-1,2-diamino-4,4-dimethyl-4-silacyclopentane)platinum (II) (as obtained in Example 1) in 100 ml of tetrahydrofuran was added a solution of 1.56 g (5.00 mmol) of silver sulfate in 400 ml of water and the resulting mixture was stirred in the dark atmosphere at 25° C. for 16 hours. The resulting precipitate of silver chloride was filtered off, then the filtrate was evaporated in vacuo and the residue was crystallized with acetone. The crystals were filtered, washed with acetone and dried in vacuo to afford 2.00 g (91.7%) of the desired compound as yellow crystals.

Melting point: 215°–225° C. (dec.).

FAB-MS (m/z): 435(M+, $^{194}$Pt), 436 [(M+1)+, $^{195}$Pt], 437 [(M+2)+, $^{196}$Pt].

IR (KBr) cm$^{-1}$: 3430, 3250, 3200 (NH$_2$), 2956, 2900 (CH), 1620, 1560 (NH$_2$), 1120 (S=O), 1254, 848 (C—Si).

Elementary analysis (C$_6$H$_{16}$N$_2$O$_4$SSiPt.H$_2$O): Cal.: C, 15.89; H, 4.00; N, 6.18. Found: C, 15.98; H, 4.05; N, 6.04.

EXAMPLE 6

Sulfato(trans-1,2-diamino-4,4-dimethyl-4-silacyclohexane)platinum (II)

This compound was prepared by the similar procedure as in the case of Example 5, except for the treatment with cis-dichloro(trans-1,2-diamino-4,4-dimethyl-4-silacyclohexane)platinum (II) (2.09 g, 5.00 mmol) instead of cis-dichloro(trans-1,2-diamino-4,4-dimethyl-4-silacyclopentane)platinum (II). The yield was 2.00 g (90.6%) as pale yellow crystals.

Melting point: 240°–250° C. (dec.).

FAB-MS (m/z): 449(M+, $^{194}$Pt), 450 [(M+1)+, $^{195}$Pt], 451 [(M+2)+, $^{196}$Pt].

IR (KBr) cm$^{-1}$: 3426, 3184 (NH$_2$), 2946 (CH), 1627 (NH$_2$), 1255, 845 (C—Si), 1119 (S=O).

Elementary analysis (C$_7$H$_{18}$N$_2$O$_4$SSiPt): Cal.: C, 17.98; H, 4.31; N, 5.99. Found: C, 17.98; H, 4.08; N, 5.67.

EXAMPLE 7

Sulfato(trans-1,2-diamino-4-trimethylsilylcyclohexane)platinum (II)

This compound was prepared by the similar procedure as in the case of Example 5, except for the treatment with cis-dichloro(trans-1,2-diamino-4-trimethylsilylcyclohexane)platinum (II) (2.26 g, 5.00 mmol) instead of cis-dichloro(trans-1,2-diamino-4,4-dimethyl-4-silacyclopentane)platinum (II). The yield was 1.55 g (64.8%) as pale yellow crystals.

Melting point: 235°–245° C. (dec.).

FAB-MS (m/z): 476(M+, $^{194}$Pt), 477 [(M+1)+, $^{195}$Pt], 478 [(M+2)+, $^{196}$Pt].

IR (KBr) cm$^{-1}$: 3430, 3200 (NH$_2$), 3080, 2935, 2860 (CH), 1250 (C—Si), 1125 (S=O).

Elementary analysis (C$_9$H$_{22}$N$_2$O$_4$SSiPt.H$_2$O): Cal.: C, 21.81; H, 4.88; N, 5.65. Found: C, 22.20; H, 5.13; N, 4.96.

EXAMPLE 8

Sulfato[bis(aminomethyl)dimethylsilane]platinum (II)

This compound was prepared by the similar procedure as in the case of Example 5, except for the treatment with cis-dichloro[bis(aminomethyl)dimethylsilane]platinum (II) (1.92 g, 5.00 mmol) instead of cis-dichloro(trans-1,2-diamino-4,4-dimethyl-4-silacyclopentane)platinum (II). The yield was 1.83 g (85.4%) as pale yellow crystals.

Melting point: 200°–205° C. (dec.).
FAB-MS (m/z): 409(M+, $^{194}$Pt), 410 [(M+1)+, $^{195}$Pt], 411 [(M+2)+, $^{196}$Pt].
IR (KBr) cm$^{-1}$: 3474, 3222 (NH$_2$), 2952, 2902 (CH), 1598 (NH$_2$), 1258, 840 (C—Si), 1113 (S=O).
Elementary analysis (C$_4$H$_{14}$N$_2$O$_4$SSiPt.H$_2$O): Cal.: C, 11.24; H, 3.77; N, 6.55. Found: C, 11.38; H, 3.51; N, 6.33.

EXAMPLE 9

Oxalato(trans-1,2-diamino-4,4-dimethyl-4-silacyclopentane)platinum (II)

To a suspension of 1.13 g (2.50 mmol) of sulfato(trans-1,2-diamino-4,4-dimethyl-4-silacyclopentane)platinum (II) (as obtained in Example 5) in 70 ml of water was added 790 mg (2.50 mmol) of barium hydroxide and the resulting mixture was stirred at 20° C. for 1 hour. The resulting precipitate of barium sulfate was filtered off, then 315 mg (2.50 mmol) of oxalic acid was washed to the filtrate and the mixture was stirred at 20° C. for 2 hours. The reaction mixture was evaporated in vacuo and the residue was crystallized with acetone. The crystals were filtered, washed with acetone and dried in vacuo to afford 910 mg (85.6%) of the desired compound as colorless crystals.

Melting point: 275°–283° C. (dec.).
FAB-MS (m/z): 427(M+, $^{194}$Pt), 428 [(M+1)+, $^{195}$Pt], 429 [(M+2)+, $^{196}$Pt].
IR (KBr) cm$^{-1}$: 3438, 3228 (NH$_2$), 2956, 2905 (CH), 1708, 1660 (C=O), 1588 (NH$_2$), 1254, 849 (C—Si).
Elementary analysis (C$_8$H$_{16}$N$_2$O$_4$SiPt.½H$_2$O): Cal.: C, 22.02; H, 3.93; N, 6.42. Found: C, 22.03; H, 3.66; N, 6.38.

EXAMPLE 10

Oxalato[bis(aminomethyl)dimethylsilane]platinum (II)

This compound was prepared by the similar procedure as in the case of Example 9, except for the treatment with sulfato[bis(aminomethyl)dimethylsilane]platinum (II) (1.07 g, 2.50 mmol) instead of sulfato(-trans-1,2-diamino-4,4-dimethyl-4-silacyclopentane]platinum (II). The yield was 790 mg (78.9%) as colorless crystals.

Melting point: 210°–230° C. (dec.).
FAB-MS (m/z): 401(M+, $^{194}$Pt), 402 [(M+1)+, $^{195}$Pt], 403 [(M+2)+, $^{196}$Pt].
IR (KBr) cm$^{-1}$: 3440, 3216 (NH$_2$), 1696, 1671 (C=O), 1253, 848 (C—Si).
Elementary analysis (C$_6$H$_{14}$N$_2$O$_4$SiPt): Cal.: C, 17.95; H, 3.52; N, 6.98. Found: C, 18.29; H, 3.46; N, 6.59.

EXAMPLE 11

1,1-Cyclobutanedicarboxylato(trans-1,2-diamino-4,4-dimethyl-4-silacyclopentane)platinum (II)

This compound was prepared by the similar procedure as in the case of Example 9, except for the treatment with 1,1-cyclobutanedicarboxylic acid (360 mg, 2.50 mmol) instead of oxalic acid. The yield was 1.03 g (85.2%) as colorless crystals.

Melting point: 295°–305° C. (dec.).
FAB-MS (m/z): 481(M+, $^{194}$Pt), 482 [(M+1)+, $^{195}$Pt], 483 [(M+2)+, $^{196}$Pt].
IR (KBr) cm$^{-1}$: 3440, 3200 (NH$_2$), 2954 (CH), 1639, 1619 (C=O), 1256, 848 (C—Si).
Elementary analysis (C$_{12}$H$_{22}$N$_2$O$_4$SiPt): Cal.: C, 29.93; H, 4.61; N, 5.82. Found: C, 29.65; H, 4.41; N, 5.66.

EXAMPLE 12

1,1-Cyclobutanedicarboxylato[bis(aminomethyl)dimethylsilane]platinum (II)

This compound was prepared by the similar procedure as in the case of Example 10, except for the treatment with 1,1-cyclobutanedicarboxylic acid (360 mg, 2.50 mmol) instead of oxalic acid. The yield was 880 mg (77.3%) as colorless crystals.

Melting point: 280°–300° C. (dec.).
FAB-MS (m/z): 455(M+, $^{194}$Pt), 456 [(M+1)+, $^{195}$Pt]. 457 [(M+2)+, $^{196}$Pt].
IR (KBr) cm$^{-1}$: 3440, 3240 (NH$_2$), 2950 (CH), 1625 (C=O), 1255, 848 (C—Si).
Elementary analysis (C$_{10}$H$_{20}$N$_2$O$_4$SiPt): Cal.: C, 26.37; H, 4.43; N, 6.15. Found: C, 26.58; H, 4.29; N, 6.11.

EXAMPLE 13

Glycolato(trans-1,2-diamino-4,4-dimethyl-4-silacyclopentane)platinum (II)

This compound was prepared by the similar procedure as in the case of Example 9, except for the treatment with glycolic acid (190 mg, 2.50 mmol) instead of oxalic acid. The yield was 1.05 g (98.4 %) as colorless crystals:

Melting point: 190°–205° C. (dec.).
FAB-MS (m/z): 413(M+, $^{194}$Pt), 414 [(M+1)+, $^{195}$Pt], 415 [(M+2)+, $^{196}$Pt].
IR (KBr) cm$^{-1}$: 3410, 3194 (NH$_2$), 2956, 2905 (CH), 1602 (C=O), 1253, 847 (C—Si).
Elementary analysis (C$_8$H$_{18}$N$_2$O$_3$SiPt): Cal.: C, 23.24; H, 4.39; N, 6.78. Found: C, 23.52; H, 4.55; N, 6.50.

EXAMPLE 14

Glycolato[bis(aminomethyl)dimethylsilane]platinum (II)

This compound was prepared by the similar procedure as in the case of Example 10, except for the treatment with glycolic acid (190 mg, 2.50 mmol) instead of oxalic acid. The yield was 725 mg (75.0%) as colorless crystals.

Melting point: 185°–205° C. (dec.).
FAB-MS (m/z): 387(M+, $^{914}$Pt), 388 [(M+1)+, $^{195}$Pt], 389 [(M+2)+, $^{196}$Pt].
IR (KBr) cm$^{-1}$: 3410, 3190 (NH$_2$), 2950, 2900 (CH), 1600 (C=O), 1253, 847 (C—Si).
Elementary analysis (C$_6$H$_{16}$N$_2$O$_3$SiPt): Cal.: C, 18.60; H, 4.16; N, 7.23. Found: C, 18.35; H, 4.33; N, 7.00.

EXAMPLE 15

Borato(trans-1,2-diamino-4,4-dimethyl-4-silacyclopentane)platinum (II)

This compound was prepared by the similar procedure as in the case of Example 9, except for the treatment with boric acid (155 mg, 2.50 mmol) instead of oxalic acid. The yield was 865 mg (86.7%) as colorless crystals.

Melting point: 190°–200° C. (dec.)

FAB-MS (m/z): 367 (M-32, 194 Pt), 368 [(M-31), 195 Pt], 369 [(M-30), 196 Pt].

IR (KBr) cm$^{-1}$: 3430, 3220 (NH$_2$), 2950, 2900 (CH), 1600 (C=O), 1250, 840 (C-Si)

Elementary analysis (C$_6$H$_{17}$BN$_2$O$_3$SiPt.4H$_2$O): Cal.: C, 15.29; H, 5.35; N, 5.94. Found: C, 15.08; H, 5.25; N, 5.95.

EXAMPLE 16

1-Butaneborato(trans-1,2-diamino-4,4-dimethyl-4-silacyclopentane) platinum (II)

This compound was prepared by the similar procedure as in the case of Example 9, except for the treatment with 1-butaneboric acid (255 mg, 2.50 mmol) instead of oxalic acid. The yield was 760 mg (69.3%) as colorless crystals.

Melting point: 210°–215° C. (dec.).

IR (KBr) cm$^{-1}$: 3440, 3194 (NH$_2$), 2950, 2920, 2864 (CH), 1600 (C=O), 1250, 840 (C-Si).

Elementary analysis (C$_{10}$H$_{25}$BN$_2$O$_2$SiPt): Cal.: C, 27.34; H, 5.74; N, 6.38. Found: C, 27.24; H, 6.61; N, 6.73.

EXAMPLE 17

Malonato(trans-1,2-diamino-4,4-dimethyl-4-silacyclopentane) platinum (II)

To a suspension of 1.23 g (3.00 mmol) of cis-dichloro(trans-1,2-diamino-4,4-dimethyl-4-silacyclopentane)platinum (II) (as obtained in Example 1) in 50 ml of tetrahydrofuran was added a solution of 1.02 g (6.00 mmol) of silver nitrate in 150 ml of water and the resulting mixture was stirred at 25° C. in the dark atmosphere for 16 hours.

The resulting precipitate of silver chloride was filtered off, then 444 mg (3.00 mmol) of disodium malonate was added to the filtrate and the mixture was stirred at 10° to 20° C. for 18 hours. The resulting precipitate was filtered and dried in vacuo to afford 810 mg (61.4%) of the desired compound as colorless crystals.

Melting point: 285°–295° C. (dec.).

FAB-MS (m/z): 441 (M$^{30}$, 194 Pt), 442 [(M+1)$^+$, 195 Pt], 443 [(M+2)$^+$, 196 Pt].

IR (KBr) cm$^{-1}$: 3422, 3172 (NH$_2$), 1670, 1638 (C=O), 1254, 850 (C—Si).

Elementary analysis (C$_9$H$_{18}$N$_2$O$_4$SiPt): Cal.: C, 24.49; H, 4.11; N, 6.35. Found: C, 24.03; H, 4.10; N, 6.20.

EXAMPLE 18

Selenito(trans-1,2-diamino-4,4-dimethyl-4-silacyclopentane) platinum (II)

This compound was prepared by the similar procedure as in the case of Example 5, except for the treatment with silver selenite (1.72 g, 5.00 mmol) instead of silver sulfate. The yield was 1.98 g (85.0%) as pale yellow crystals.

Melting point: 200°–210° C. (dec.).

IR (KBr) cm$^{-1}$: 3428, 3198 (NH$_2$), 2956 (CH), 1594 (NH$_2$), 1253, 846 (C—Si).

Elementary analysis (C$_6$H$_{16}$N$_2$O$_3$SeSiPt.H$_2$O): Cal.: C, 14.88; H, 3.75; N, 5.78. Found: C, 14.59; H, 4.00; N, 5.99.

EXAMPLE 19

Selenito[bis(aminomethyl)dimethylsilane]platinum (II)

This compound was prepared by the similar procedure as in the case of Example 18, except for the treatment with cis-dichloro[bis(aminomethyl)dimethylsilane]platinum (II) (2.14 g, 5.00 mmol) instead of cis-dichloro(trans-1,2-diamino-4,4-dimethyl-4-silacyclopentane)platinum (II). The yield was 1.82 g (81.5%) as pale yellow crystals.

Melting point: 195°–215° C. (dec.).

IR (KBr) cm$^{-1}$: 3430, 3200 (NH$_2$), 2956 (CH), 1595 (NH$_2$), 1255, 848 (C—Si).

Elementary analysis (C$_4$H$_{14}$N$_2$O$_3$SeSiPt.H$_2$O): Cal.: C, 10.48; H, 3.52; N, 6.11. Found: C, 10.15; H, 3.80; N, 6.33.

PHARMACOLOGICAL TEST EXAMPLE 1

(Anti-tumor activity to L-1210 leukemia)

L-1210 leukemia cells (1×10$^5$) were intraperitoneally transplanted to CDF$_1$ male mice (age of about 5 weeks, 4 to 5 heads/group). Each of the testing compounds was intraperitoneally injected over 5 days (1 time per day) after expired 24 hours from the inoculation. Anti-tumor activity of each testing compound was determined by comparison of the mean survival time of the treated group (T) to that of the control group (C).

Results are shown in following Table 1, in which

T/C (%)=(T/C)×100.

TABLE 1

| Compound (Example No.) | Dose (mg/kg) | T/C (%) | Survivors/Total at 30th day after tumor cell inoculation |
|---|---|---|---|
| 1 | 5 | 183 | 0/5 |
|  | 10 | 173 | 0/5 |
|  | 15 | >301 | 2/4 |
|  | 20 | 218 | 0/5 |
| 2 | 1 | 133 | 0/4 |
|  | 5 | 193 | 0/4 |
|  | 10 | 180 | 0/4 |
|  | 20 | 223 | 0/4 |
| 3 | 5 | 150 | 0/4 |
|  | 10 | 172 | 0/4 |
|  | 15 | 203 | 0/4 |
|  | 20 | 206 | 0/4 |
| 10 | 15 | 144 | 0/4 |
| 15 | 3 | 164 | 0/4 |
|  | 6 | 215 | 0/4 |
|  | 10 | >294 | 2/4 |
| 16 | 5 | 163 | 0/4 |
|  | 10 | 167 | 0/4 |
|  | 15 | 170 | 0/4 |
|  | 20 | 180 | 0/4 |
| Cisplatin | 4 | 242 | 0/4 |

PHARMACOLOGICAL TEST EXAMPLE 2

(Nephrotoxicity)

The compounds were evaluated for nephrotoxicity by determining their effects on blood urea nitrogen (BUN) levels in rats.

The testing compounds, or saline for control were given intravenously to male Fisher-344 rats (age of about 5 weeks, 5 heads per group), as a single injection. The BUN values were measured on the 5th day after the dosage. Results are shown in following Table 2.

TABLE 2

| Compound (Example No.) | Dose (mg/kg) | BUN (mg/dl) |
|---|---|---|
| Control | — | 20.76 ± 0.76 |
| 5 | 6 | 21.96 ± 1.01 |
|  | 12 | 23.68 ± 1.20 |
|  | 24 | 37.48 ± 6.08 |
| 9 | 6 | 22.08 ± 0.63 |
|  | 12 | 21.48 ± 1.08 |
|  | 24 | 22.44 ± 0.58 |

TABLE 2-continued

| Compound (Example No.) | Dose (mg/kg) | BUN (mg/dl) |
|---|---|---|
| Cisplatin | 4 | 40.04 ± 2.5 |
| | 6 | 138.16 ± 13. |
| | 8 | 395.6 ± 44.0 |

PREPARATION EXAMPLE 1 (Injection)

Following ingredients were prescripted to prepare an injection in a conventional manner.

| The complex (Example 9) | 10 mg |
|---|---|
| 0.9% NaCl solution | remainder |
| | 20 ml/vial |

PREPARATION EXAMPLE 2 (Capoule)

Following ingredients were prescripted to prepare capsules in a conventional manner.

| The complex (Example 1) | 10 (mg) |
|---|---|
| Lactose | 50 |
| Potato starch | 50 |
| Crystalline cellulose | 109 |
| Magnesium stearate | 1 |
| | 220 mg/capsule |

PREPARATION EXAMPLE 3 (Granule)

Following ingredients were prescripted to prepare granules in a conventional manner.

| The complex (Example 2) | 10 (mg) |
|---|---|
| Lactose | 550 |
| Corn starch | 330 |
| Hydroxypropylcellulose | 20 |
| | 910 mg/package |

PREPARATION EXAMPLE 4 (Tablet)

Following ingredients were prescripted to prepare tablets in a conventional manner.

| The complex (Example 10) | 10 (mg) |
|---|---|
| Crystalline cellulose | 20 |
| Lactose | 41 |
| Corn starch | 30 |
| Hydroxypropylcellulose | 6 |
| Magnesium stearate | 3 |
| | 110 mg/tablet |

What is claimed is:

1. An organo-platinum complex selected from the formulas

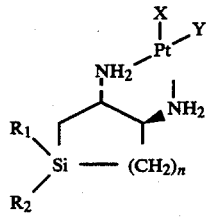

wherein X and Y are independently selected from the group consisting of halogen, sulfate, nitrate, selenite, chloroacetate, pyruvate and glucolate, or X and Y taken together are selected from the group consisting of oxalate, malonate, hydroxymalonate, phthalate and 1,1-cyclobutanedicarboxylate; $R_1$, $R_2$ and $R_3$ are independently selected from the group consisting of lower alkyl and phenyl; and n is 0 or 1.

2. An organo-platinum complex as claimed in claim 1, wherein said complex is cis-dichloro(trans-1,2-diamino-4,4-dimethyl-4-silacyclopentane)platinum (II).

3. An organo-platinum complex as claimed in claim 1, wherein said complex is sulfato(trans-1,2-diamino-4,4-dimethyl-4-silacyclopentane)platinum (II).

4. An organo-platinum complex as claimed in claim 1, wherein said complex is borato(trans-1,2-diamino-4,4-dimethyl-4-silacyclopentane)platinum (II).

5. An organo-platinum complex as claimed in claim 1, wherein said complex is 1-butaneborato(trans-1,2-diamino-4,4-dimethyl-4-silacyclopentane)platinum (II).

6. An organo-platinum complex as claimed in claim 1, wherein said complex is oxalato(trans-1,2-diamino-4,4-dimethyl-4-silacyclopentane)platinum. (II).

7. An organo-platinum complex as claimed in claim 1, wherein said complex is glycolato(trans-1,2-diamino-4,4-dimethyl-4-silacyclopentane)platinum (II).

8. An organo-platinum complex as claimed in claim 1, wherein said complex is 1,1-cyclobutanedicarboxylato(-trans-1,2-diamino-4,4-dimethyl-4-silacyclopentane)-platinum (II).

9. An organo-platinum complex as claimed in claim 1, wherein said complex is malonato(trans-1,2-diamino-4,4-dimethyl-4-silacyclopentane)platinum (II).

10. An organo-platinum complex as claimed in claim 1, wherein said complex is selenito(trans-1,2-diamino-4,4-dimethyl-4-silacyclopentane)platinum (II).

11. An organo-platinum complex as claimed in claim 1, wherein said complex is cis-dichloro(trans-1,2-diamino-4,4-dimethyl-4-silacyclohexane)platinum (II).

12. An organo-platinum complex as claimed in claim 1, wherein said complex is sulfato(trans-1,2-diamino-4,4-dimethyl-4-silacyclohexane)platinum (II).

13. An organo-platinum complex as claimed in claim 1, wherein said complex is cis-dichloro(trans-1,2-diamino-4-trimethylsilylcyclohexane)platinum (II).

14. An organo-platinum complex as claimed in claim 1, wherein said complex is sulfato(trans-1,2-diamino-4-trimethylsilylcyclohexane)platinum (II).

15. An organo-platinum complex as claimed in claim 1, wherein said complex is cis-dichloro[bis(aminomethyl)dimethylsilane]platinum (II).

16. An organo-platinum complex as claimed in claim 1, wherein said complex is sulfato[bis(aminomethyl)-dimethylsilane]platinum (II).

17. An organo-platinum complex as claimed in claim 1, wherein said complex is oxalato[bis(aminomethyl)-dimethylsilane]platinum (II).

18. A organo-platinum complex as claimed in claim 1, wherein said complex is 1,1-cyclobutanedicarboxylato[-bis(aminomethyl)dimethylsilane]platinum (II).

19. An organo-platinum complex as claimed in claim 1, wherein said complex is glycolato[bis(aminomethyl)-dimethylsilane]platinum (II).

20. An organo-platinum complex as claimed in claim 1, wherein said complex is selenito[bis(aminomethyl)-dimethylsilane]platinum (II).

21. An anti-tumor composition comprising an anti-tumor effective amount of the organo-platinum complex of claim 1 together with a pharmaceutically acceptable carrier.

22. An anti-tumor composition as claimed in claim 21, wherein said organo-platinim complex is those selected from the group consisting of
- (a) cis-dichloro(trans-1,2-diamino-4,4-dimethyl-4-silacyclopentane)platinum (II),
- (b) sulfato(trans-1,2-diamino-4,4-dimethyl-4-silacyclopentane)platinum (II),
- (c) borato(trans-1,2-diamino-4,4-dimethyl-4-silacyclopentane)platinum (II),
- (d) 1-butaneborato(trans-1,2-diamino-4,4-dimethyl-4-silacyclopentane)platinum (II),
- (e) oxalato(trans-1,2-diamino-4,4-dimethyl-4-silacyclopentane)platinum (II),
- (f) glycolato(trans-1,2-diamino-4,4-dimethyl-4-silacyclopentane)platinum (II),
- (g) 1,1-cyclobutanedicarboxylato(trans-1,2-diamino-4,4-dimethyl-4-silacyclopentane)platinum (II),
- (h) malonato(trans-1,2-diamino-4,4-dimethyl-4-silacyclopentane)platinum (II),
- (i) selenito(trans-1,2-diamino-4,4-dimethyl-4-silacyclopentane)platinum (II),
- (j) cis-dichloro(trans-1,2-diamino-4,4-dimethyl-4-silacyclohexane)platinum (II),
- (k) sulfato(trans-1,2-diamino-4,4-dimethyl-4-silacyclohexane)platinum (II),
- (l) cis-dichloro(trans-1,2-diamino-4-trimethylsilylcyclohexane)platinum (II),
- (m) sulfato(trans-1,2-diamino-4-trimethylsilylcyclohexane)platinum (II),
- (n) cis-dichloro[bis(aminomethyl)dimethylsilane]platinum (II),
- (o) sulfato[bis(aminomethyl)dimethylsilane]platinum (II),
- (p) oxalato[bis(aminomethyl)dimethylsilane]platinum (II),
- (q) 1,1-cyclobutanedicarboxylato[bis(aminomethyl)dimethylsilane]platinum (II),
- (r) glycolato[bis(aminomethyl)dimethylsilane]platinum (II), and
- (s) selenito[bis(aminomethyl)dimethylsilane]platinum (II).

* * * * *